United States Patent [19]

Drushel

[11] 4,252,021

[45] Feb. 24, 1981

[54] FLUID SAMPLING DEVICE

[76] Inventor: Ronald H. Drushel, 224 Friar Tuck, Baton Rouge, La. 70815

[21] Appl. No.: 82,894

[22] Filed: Oct. 9, 1979

[51] Int. Cl.³ .............................................. G01N 1/10
[52] U.S. Cl. .......................... 73/422 TC; 73/425.4 R; 137/614
[58] Field of Search .................. 73/422 TC, 425.4 R, 73/422 R; 137/572, 588, 613, 614, 798

[56] References Cited

U.S. PATENT DOCUMENTS

| 3,842,677 | 10/1974 | Bufkin et al. | 73/422 R X |
| 4,174,632 | 11/1979 | Jansen | 73/422 R |

Primary Examiner—Jerry W. Myracle
Attorney, Agent, or Firm—Llewellyn A. Proctor

[57] ABSTRACT

Apparatus for sampling fluids, i.e. liquids or gases, or both, from a supply source. The apparatus comprises an adapter unit inclusive of a pair of tubular sections, or members, detachably engaged one with the other, each contains communicating inlet and outlet channels, respectively, and each has valve elements for opening and closing the channels. One tubular section of the adapter unit can thus be located at the fluid supply source, and the other adapted for connection to a portable supply container such that, when the valve elements are opened, fluid from the supply source will fill the container and, after the container is filled, the valve elements of the two sections of the adapter unit can be closed to shut off the fluid supply as well as close off fluid communication between the two tubular sections. The two tubular sections, by thus isolating the fluid supply source from the container, can then be separated so that the first tubular section remains with the fluid supply source, while the second tubular section remains with the detached, filled portable supply container.

8 Claims, 3 Drawing Figures

FLUID SAMPLING DEVICE

In commercial operations it is necessary, on a routine basis to obtain fluid samples, or specimens, from process streams. As is well known, many of these streams contain extremely hazardous, or toxic materials which cannot be permitted to contaminate the working environment. It is absolutely essential that personnel not be exposed to these materials, inclusive of course of the personnel who are required to sample the process streams.

Accordingly, it is the primary objective of the present invention to obviate this and other problems, particularly by providing a single point for connection of a sample cylinder to a process stream.

It is a specific object of this invention to provide apparatus inclusive of a supply container which can be conveniently, easily and quickly connected in-line with the process stream, and similarly disconnected without interruption of the flow during withdrawal of the sample in filling the supply container.

A more specific object is to provide low budget, low maintenance apparatus with suitable connections and valving for filling, discharging, by-passing, sweeping gas, and purge venting via a single process connection point to a process stream.

These objects and others are achieved in accordance with the apparatus of the present invention which comprises an adapter unit which includes a pair of tubular sections detachably engaged one section with the other, each of which contains communicating inlet and outlet channels, respectively, and each has valve means for opening and closing said channels. One of the tubular sections can be located at a fluid supply source, and the other adapted to carry a portable supply container such that, when the valve means are opened, fluid from the supply source can be conveyed via the communicating inlet channels of the two sections of the adapter unit to the container and, after the container is filled, the valve means can be closed to shut off and separate the fluid supply source from the filled container, as well as close off fluid communication between the two tubular sections. The two tubular sections can then be separated so that the first tubular section remains at the fluid supply source, while the second section remains with the detached, filled portable supply container.

Suitably, the tubular sections of the adapter unit are threadably engaged one with the other, and one is engaged to the supply container. Preferably, one tubular section of the adapter unit is a male member, and the other a female member. One section, suitably the male section, is located at the fluid supply source while the other is engagably with the portable supply container. The supply container is constituted of a thick walled vessel capable of withstanding a relatively high pressure, and one side is open to provide a single location of attachment, suitably threadable engagement with one of the tubular sections of the adapter unit whereby fluid from the supply source can be conveyed to said container, and returned from the container to the supply source through the same location of attachment.

These and other features and advantages will be better understood by reference to the following detailed description and to the accompanying drawings to which reference is made in the description.

Referring to the drawings.

Figure 1:
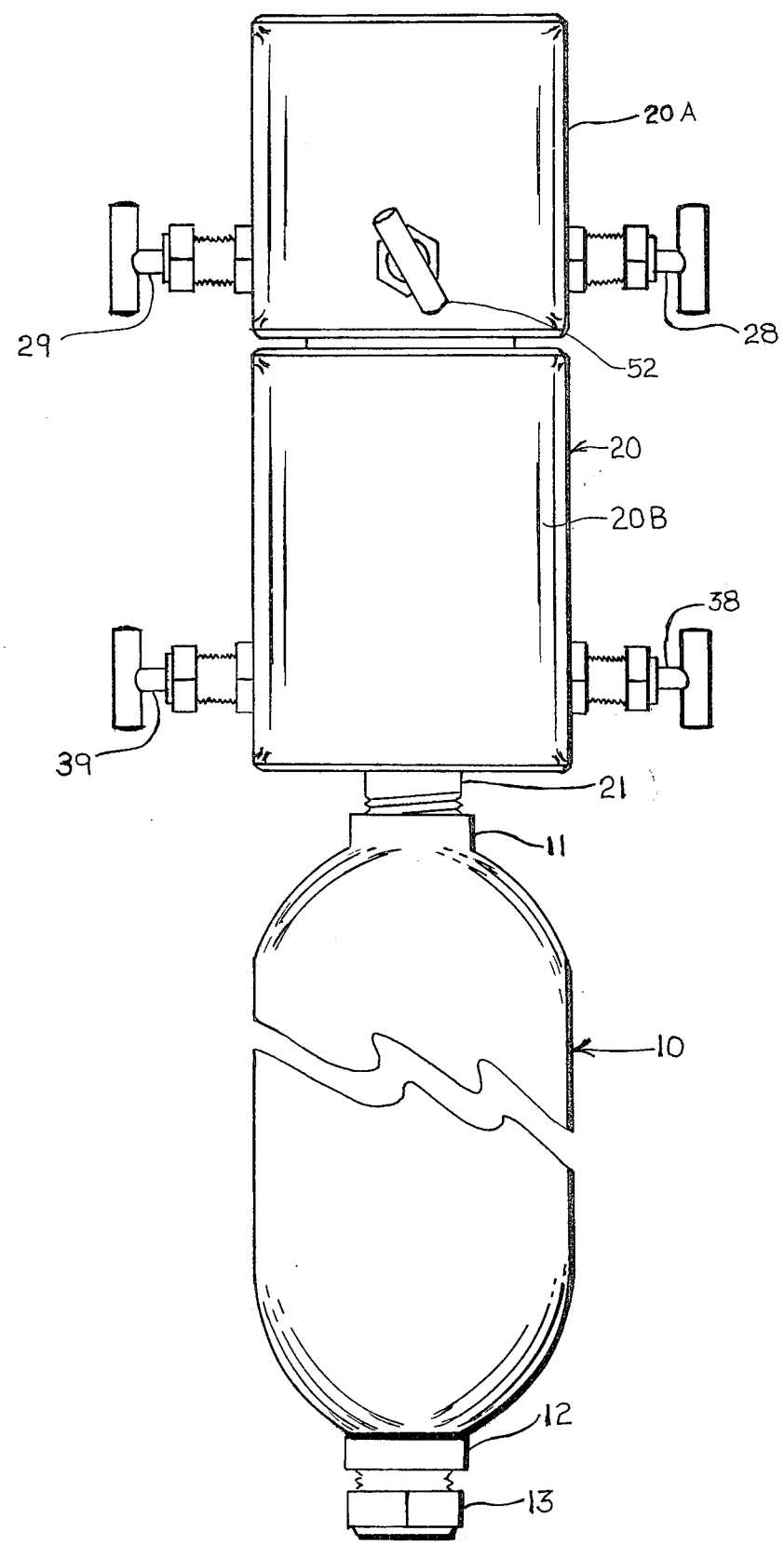
FIG. 1 depicts a side elevation view of an adapter unit, and sample cylinder affixed thereto as used for the withdrawal and sampling of fluid from a process stream.

Referring to FIG. 1 there is shown a sample container, or cylinder 10 which threadably engaged with an adapter unit 20. The sample cylinder is constituted of a hollow vessel, the enclosing thick side wall of which forms an elongated substantially cylindrical, or tubular central section. Gradually sloping thick end walls provide an over-all, elongated bulb shaped cylinder. One end wall of the sample cylinder 10 is necessarily provided with an opening, and this opening is provided with a tubular nozzle, or projection 11 which is internally threaded for engagement with the externally threaded nozzle projection 21 of the adapter unit. The opposite end of the sample cylinder 10 is also optionally provided with an opening, and it is provided with a similar internally threaded nozzle projection 12 for the attachment, or engagement therewith of various recording devices, e.g. thermometers, pressure gauges, or the like; or valve as may be desired for emptying the filled sample cylinder. For convenience, as shown in the drawing, this latter opening provided within the nozzle projection 12 is closed by an externally threaded plug 13.

Figure 2:
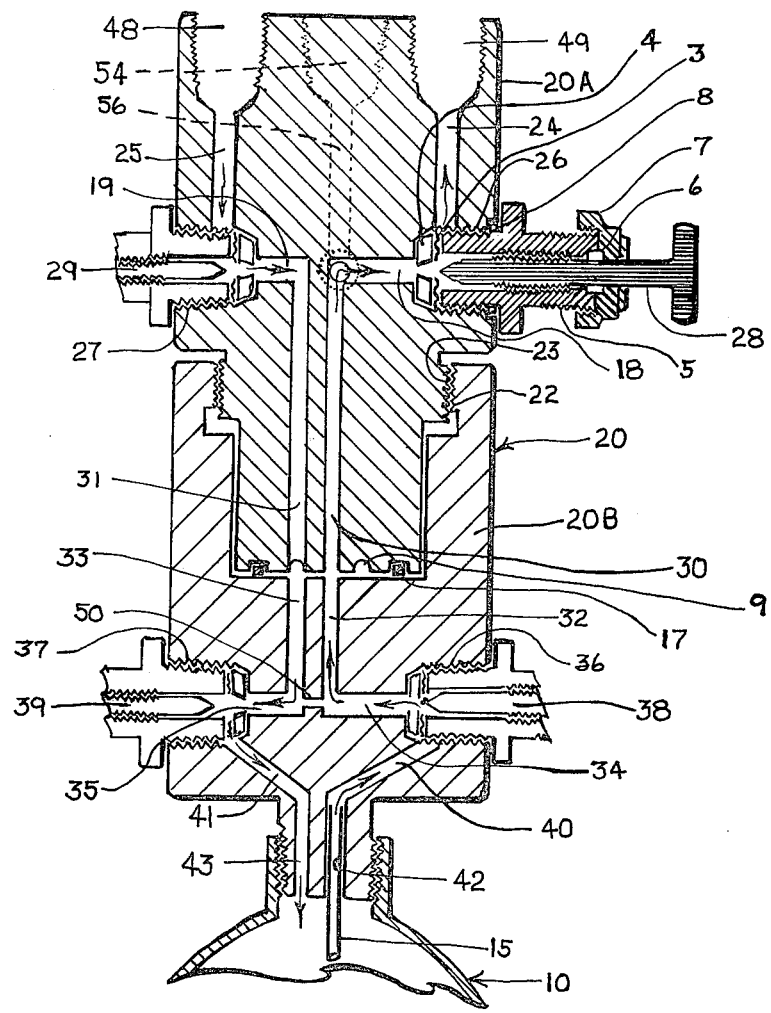
FIG. 2 is a section view of the adapter unit.

The adapter unit 20, as best shown by reference to FIG. 2, is constituted of two tubular sections, a male section 20A and a female section 20B. The sections 20A, 20B are detachably engaged one member to the other via external threads 23 located near the forward end of the male section 20A and the internal threads 22 located at the rearward terminal end of the female section 20B.

The rearward portion of male section 20A, it will be observed, is provided with a pair of parallel channels 24, 25, each of which is connected to a valve seat opening 26, 27, respectively, within which valve stems 28, 29 can be seated. The channels 24, 25, it will be further observed connect through the valve seat opening 26, 27, and conduit segments 18, 19, with channels 30, 31, respectively. The forward face of the member 20A is provided with a seating surface for an O-ring, or gasket 17, which forms a seal when the face of member 20A is pressed tightly against the rearward face of member 20B. Referring further to female member 20B, it will be observed that this member too is provided with a pair of parallel channels 32, 33 which connect via perpendicularly intersecting channels 34, 35 to valve seat opening 36, 37 within which valve stems 38, 39 can be seated. The channels 34, 35 in turn are connected through valve seat openings 36, 37 with curved channels 40, 41 and 42, 43, respectively, these latter segments of conduit of which lead directly into the sample container 10. Thus, it will be observed that when valve stems 28, 29, 38, 39 are in an unseated position, and members 20A, 20B are tightly joined, a continuous conduit is provided by channels 25, 19, 31, 33, 41 and 43 for supplying fluid from a process for entry into sample container 10. Conversely, it will be apparent that a path is provided via conduits 42, 40, 34, 32, 30, 18, 24. Channels 31, 33 within the male member and female member, respectively, remain in permanent communication when these members are joined via means of groove 9 located in the face of the male member 20A, concentric with channel 30 and passing through the terminal end of channel 31.

In its preferred aspect, the channel 42 which opens into the supply cylinder 10 is of larger internal diameter than that of channel 43, and a tubular conduit, or dipleg 15 is mounted therein and extended into the supply cylinder 10. The internal diameter of the dipleg is of smaller internal diameter than the internal diameter of channel 43 to provide a slight backpressure inside the supply cylinder 19, thus suppressing gas separation within the tube where a gaseous mixture of relatively low and high volatility components are contained in the gaseous mixture.

The design and function of the several valve stems 28, 29, 38, 39 (and 51, 52 subsequently discussed), the manner in which they are mounted in the adapter unit 20, and the nature of their seating are quite similar. Each stem per se, e.g. of valve stem 28, is externally threaded and threadably engaged with the internally threaded wall of a tubular member 5 which is tightly fitted via threadable engagement within the valve seat opening 26 and retained therein via the retainer ring 8. The stem 28 per se is passed through an opened centered bonnet 7 threadably engaged to the top of the tubular member 5, and packing 6, the lowermost end thereof lying near an annular shaped seal 4 retained in peace via an open centered retainer ring 3. The lower terminal end of the valve stem is shaped to fit tightly into the lower part of the valve seat, and seal 4, to close off flow through the respective junctions of the paired conduit segments 18, 24 to close off flow, or unseated to permit flow. Each valve stem is rotatable mounted within its respective valve seat, and movable upwardly or downwardly therein by rotation.

Figure 3:
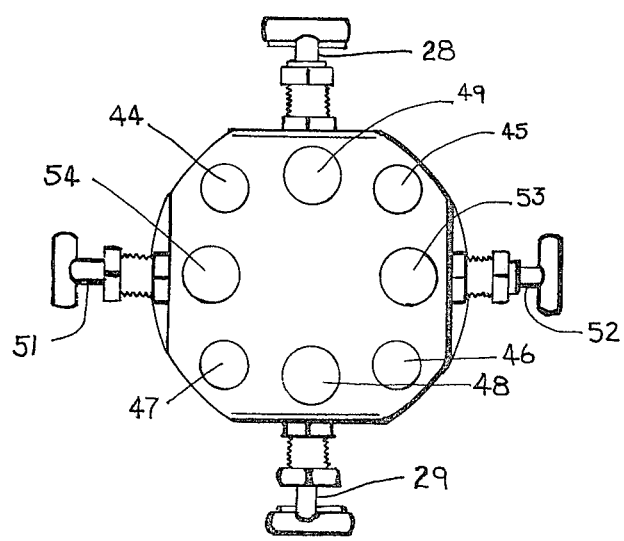
FIG. 3 is a rear end view of the adapter unit.

In mounting the adapter unit 20, the male section 20A, coupled tightly with the female section 20B with the supply cylinder affixed, thereto, is mounted via the projection of bolts or screws through mounting holes 44, 45, 46, 47 (FIG. 3) to secure said member in place upon a process unit, e.g. conduit, reactor, etc. The valve stems 28, 29, 38, 39 are rotated to unseat there members. An input fluid, gas, liquid or admixture thereof, from the unit is then passed into the input opening 48, the fluid passing into the supply container 10, via channels 25, 19, 31, 33, 35, 41, 43. Fluid from the supply container flows through the dipleg 15, and channels 42, 40, 34, 32, 30, 18 and 24 to return to the process unit via output opening 49. When the supply container 10 is filled with fluid, and contains a representative specimen, the valve stems 28, 29, 38, 39 are rotated and the stems reseated to close off the supply of fluid from the process, and to seal the sample container 10. This done, the female member 20B with the filled supply container 10 in place, can be removed from the process unit and transported to another site for removal and analysis of the fluid speciman. The male member 20A of the adapter unit is left in place on process unit.

In an optional, and preferred construction, the adapter unit 20 is also provided with a flush, purge, or evacuation feature. Referring to FIG. 2 it will thus be observed that a small connecting port 50 can be located between conduits 32, 33 and that two additional valve stems 51, 52 are provided. In accordance with this feature, with female section 20B tightly in place, valve stems 38, 39 are screwed tightly in place to close off the parallel conduits leading to the supply cylinder 10. Valve stems 51, 52 are then unseated, e.g., so that fluid passed into input opening 53 will ingress from the process inwardly through conduits 55 (not shown), 31 and 50, then discharged via port 50 for return via conduits 32, 30, 56 via output opening 54 to the process unit. On completion of the purge, or evacuation, the valve stems 51, 52 are reseated to close off this circuit.

It is apparent that various modifications and changes, such as in the absolute or relative dimensions of the parts, materials used and the like, as well as in the suggested mode of sampling fluids, can be made without departing the spirit and scope of the invention.

Having described the invention what is claimed is:

1. In apparatus for sampling fluid from a source of supply, and for the collection of said fluid specimen in a container, the improvement comprising An adapter unit which includes two tubular sections detachably engaged one section with the other,
   a first tubular section for location at the fluid supply source which contains a fluid supply inlet and outlet channels, respectively, associated therewith, and valve means for opening and closing each of said channels,
   a second tubular section which contains inlet and outlet channels, respectively, which can be aligned with said inlet and outlet channels, respectively, of said first section to provide continuous conduits when the two sections are engaged, the inlet and outlet channels of said second tubular section leading into said sample container, and valve means for opening and closing each of said channels of said second section, Whereby with all valve means opened, fluid from the supply source can be passed to the container through the fluid supply inlet channel of said first tubular section and the aligned inlet channel of said second tubular section of the adapter unit, and returned from the container to the supply source through the outlet channel of said second tubular section and the aligned outlet channel of said first tubular section of the adapter unit, and when the container is filled and, all valve means closed, the second tubular section with the container can be detached from said first tubular section and the isolated container with its fluid specimen can be transported to a desired site.

2. The Apparatus of claim 1 wherein the first tubular section and the second tubular section of the adapter unit are adjoined one to the other via threadable engagement, and the container is adjoined to the second tubular section via threadable engagement.

3. The Apparatus of claim 2 wherein the first tubular section is a male member, and the second tubular section is a female section.

4. The Apparatus of claim 1 wherein the container side of the outlet channel of said second tubular section is of smaller internal diameter than that of the container side of said second tubular section.

5. The Apparatus of claim 4 wherein the container side of the outlet channel of said second tubular section is of larger internal diameter than that of the container side of said second tubular section, but its effective internal diameter leading to the container is restricted by the presence of a tubular leg concentrically mounted therein, the dipleg being extendable into said container.

6. In Apparatus for sampling fluid from a source of supply the combination which comprises
   a sample container within which a specimen of the fluid being sampled can be contained,
   an adapter unit which includes male and female tubular sections which can be detachably engaged one section with the other,
   a male section for location at the fluid supply source which contains a fluid supply inlet and outlet, and inlet and outlet channels, respectively, associated therewith, and valve means for opening and closing each of said channels, a female section which contains inlet and outlet channels, respectively, which can be aligned with said inlet and outlet channels, respectively, of said male section to provide continuous conduits when the two sections are in engagement, the inlet and outlet channels of said female section leading into said sample container, and valve means for opening and closing each of said channels of said female section, whereby will all valve means open, fluid from the supply source can be passed to the container through the fluid supply inlet of said male member and the aligned inlet channels of said male and female sections of the adapter unit, and returned from the container to the supply source through the outlet channels of the male and female sections, and fluid output side of the male section, of the adapter unit, and when the container is filled and, with all valve means closed, the female section with the container can be detached from the male section and the isolated container with its fluid specimen can be transported to a desired site.

7. The Apparatus of claim 6 wherein the sample container is provided with an additional fluid outlet, separate and apart from that which is in communication with the said female section of the adapter unit.

8. The Apparatus of claim 7 wherein the sample container has an enclosing side wall to provide a substantially cylindrical shape, the ends walls are rounded and sloped inwardly to provide an overall elongated bulb-like appearance, and an end of the container is provided with a projecting nozzle on which said container is supported upon, and supplied with fluid from said female section of the adapter unit.

* * * * *